(12) United States Patent
Somberg et al.

(10) Patent No.: US 6,844,355 B2
(45) Date of Patent: Jan. 18, 2005

(54) OPTICALLY ACTIVE ISOMERS OF QUININE AND QUINIDINE AND THEIR RESPECTIVE BIOLOGICAL ACTION

(75) Inventors: John C. Somberg, Lake Forest, IL (US); Vasant Ranade, Libertyville, IL (US)

(73) Assignee: Academic Pharmaceuticals, Inc., Lake Bluff, IL (US)

( * ) Notice: Subject to any disclaimer, the term of this patent is extended or adjusted under 35 U.S.C. 154(b) by 0 days.

(21) Appl. No.: 10/168,919

(22) PCT Filed: Dec. 22, 2000

(86) PCT No.: PCT/US00/35213

§ 371 (c)(1),
(2), (4) Date: Oct. 30, 2002

(87) PCT Pub. No.: WO01/46188

PCT Pub. Date: Jun. 28, 2001

(65) Prior Publication Data

US 2003/0212098 A1 Nov. 13, 2003

Related U.S. Application Data

(60) Provisional application No. 60/171,952, filed on Dec. 23, 1999.

(51) Int. Cl.[7] .................. A61K 31/437; C07D 453/04
(52) U.S. Cl. .................. 514/305; 546/134; 546/112; 514/299
(58) Field of Search .................. 514/305, 299; 546/134, 112

(56) References Cited

U.S. PATENT DOCUMENTS

3,907,806 A    9/1975    Guenter et al.
3,929,795 A   12/1975    Walter et al.

FOREIGN PATENT DOCUMENTS

EP    0 000 302    1/1979

OTHER PUBLICATIONS

Barhanin et al., (1996) *Nature* 384(6604):78–80.
Bennet et al., (1995) *Nature* 376:683–685.
Busch et al., (1994) *Eur J. Pharmacol.* 264:33–37.
Catterall, (1992) *Physiol. Rev.* 72(supp):S15–S48.
Chan et al., (1991) *J. Chromatogr.* 571:291–297.
Chen et al., (1998) *Nature* 392:293–296.
Coplen et al., (1991) *Circulation* 84:527.
Drabowicz et al., (1984) "Chemical Abstracts" *Phosphorus Sulfur* 16:2676–270 (XP002165239).
Engler et al., (1985) *Helv. Chim. Acta.* 68:789–800.
Ficker et al., (1998) *Circ. Res.* 82:386–395.
Gellens et al., (1992) *Proc. Natl. Acad. Sci.* 89:554–558.
Gutzwiller et al., (1973) "Chemical Abstracts" *Helv. Chim. Acta.* 79:1494–1503 (XP002165238).
Hartmann et al. (1994) *Circ. Res.* 75:114–122.
Karle I.L. et al., (1981) *Proc. Natl. Acad. Sci.* 78:5938–5941.
Karle, J.M. (1997) *Antimicrob. Agents Chemother.* 41:791–794.
Kiehn et al. (1996) *Circulation* 94:2572–2579.
Krafte et al., (1994) *Europ. J. Pharma.* 266:245–254.
Li et al. (1996) *Circ. Res.* 78:689–696.
Sanguinetti et al., (1990) *J. Gen. Physiol.* 96:195–215.
Sanguinetti et al., (1995) *Cell* 81:299–307.
Sanguinetti et al., (1996) *Nature* 384:80–83.
Spector et al., (1996) *J. Gen. Phsyiol.* 107:611–619.
Synders et al., (1991) *Mol. Pharmacol.* 41:322–330.
Trudeau et al., (1995) *Science* 269:92–95.
Van Neuten et al. (1978) *Life Sci.* 28:453–458.
Wang et al., (1995) *Hum. Mol. Genet.* 4:1603–1607.
Willius, et al. (1942) *Proc. Staff Meet. Mayo Clin.* 17:294–296.
International Search Report for International Application PCT/US 00/35213.

Primary Examiner—Charanjit S. Aulakh
(74) Attorney, Agent, or Firm—McDonnell Boehnen Hulbert & Berghoff LLP (57) ABSTRACT

The present invention provides methods for purifying, identifying and using optically active isomers of quinine and quinidine as well as compositions comprising such optically active isomers. Such optically active isomers having desired actions on cardiac sodium and potassium channel function substantially separable from undesirable effects on GI motility can be useful for more effective therapy of cardiac arrhythmias. Also disclosed are methods for assaying the levels of such isomers present in the biological fluids.

20 Claims, 10 Drawing Sheets

| Compound | R¹ | R² | R³ | R⁴ |
|---|---|---|---|---|
| 1a | H | OH | ▬H | ⋯H |
| 1b | H | OH | ⋯H | ▬H |
| 1c | H | OH | ⋯H | ⋯H |
| 1d | H | OH | ▬H | ▬H |
| 1e | OH | H | ▬H | ▬H |
| 1f | OH | H | ▬H | ⋯H |
| 1g | OH | H | ⋯H | ▬H |
| 1h | OH | H | ▬H | ▬H |

Fig. 1

| Compound | R¹ | R² | R³ | R⁴ |
|---|---|---|---|---|
| 2a | OH | H | ▤H | ⋯H |
| 2b | OH | H | ⋯H | ▤H |
| 2c | OH | H | ⋯H | ⋯H |
| 2d | OH | H | ▤H | ▤H |
| 2e | H | OH | ▤H | ⋯H |
| 2f | H | OH | ⋯H | ▤H |
| 2g | H | OH | ⋯H | ⋯H |
| 2h | H | OH | ▤H | ▤H |

OPTICALLY ACTIVE ISOMERS OF QUININE AND QUINIDINE AND THEIR RESPECTIVE BIOLOGICAL ACTION

This application claims the benefit of U.S. Provisional Application Ser. No. 60/171,952, filed Dec. 23, 1999, which is incorporated herein by reference in its entirety.

BACKGROUND OF THE INVENTION

1. Field of the Invention

The present invention relates generally to the resolving of stereoisomers of quinidine and quinine. More particularly, the invention relates to the identification of the biological activity of the different stereoisomers of quinidine and quinine.

2. Description of the Related Art

Quinidine is the most prescribed anti-arrhythmic agent in the United States. However, the clinical utility of quinidine is limited by the adverse effect of diarrhea In addition, quinidine causes arrhythmias, especially the torsade de pointes variety that results from a long QT interval. The significant proarrhythmia (worsening of ventricular arrhythmias) associated with quinidine are possibly due to its combined effect on both the sodium depolarizing current and the potassium repolarizing current.

The first medicinal remedy for the treatment of cardiac arrhythmias is derived from the bark of the cinchona tree, indigenous to South America, where South American Indians long-used cinchona as medication. Europeans brought the remedy back from their New World explorations. Jean-Baptiste Senac, a French physician, is the first to describe the use of cinchona extract for cardiac irregularities (Willius, F A, et al., *Proc. Staff Meet. Mayo Clin,* 1942, 17, 294–296). Subsequently, a ship's captain with the medical condition auricular (atrial) fibrillation is seen by one of the leading European cardiologists, Professor Wenckebach, who had no treatment for the condition (Wenckebach, K F. *Die unregelmassige Herztatigkeit und ihre klinische bedeutung.* W. Engelmann, Leipzig, 1914). The ship's captain showed Wenckebach how the bark of the cinchona could control the cardiac irregularity. Following this, Wenckebach popularized the use of the cinchona extract for arrhythmia therapy. The principal active anti-arrhythmic ingredient of cinchona, quinidine, is identified in 1918 by the American chemist, Frey (Frey, W. et al., *Wien. Klin. Wschr.,* 1918, 55, 849–853).

While quinidine is still actively prescribed in the United States, its use is severely limited by a number of problems. The drug prolongs the QT interval on the electrocardiogram, in a very heterogeneous way, creating a predisposition leading to the development of cardiac arrhythmias, especially Torsade de pointes, which is a rapid ventricular tachycardia. A number of studies have indicated that patients taking quinidine are at a higher risk for death than those not taking quinidine (e.g., Coplen S. E, et al., *Efficacy and safety of quinidine therapy for maintenance of sinus rhythm after cardioversion; Circulation* 1991; 84:527). Quinidine is also limited by severe GI disturbances with the most limiting side-effect being diarrhea. Recent research has shown that the drug affects both the cardiac sodium channel and the cardiac potassium channel, making quinidine a very complex "mixed" action agent (Krafte D. S., et al., *Europ J Pharma* 1994; 266, 245–254; Snyders D. J., et al., *Molecular Pharma,* 1991 41:322–330).

The anti-arrhythmic action of quinidine is thought to be due to its effect on the sodium channel. Quinidine is classified as a Vaughn Williams type Ia anti-arrhythmic. However, its prolongation of the QT interval due to APD (action potential duration) prolongation is not well understood. Subsequently, quinidine is found to show a significant effect in blocking the potassium repolarizing current, thus possessing type III Vaughn Williams (classification) effect. More recently the prolongation of APD has been found to be both an anti-arrhythmic action, as well as being the basis for the development of a rapid ventricular tachycardia with unique morphology called Torsade de Pointes ventricular tachycardia. Additionally, two potassium channels have been reported to be critically involved in human repolarization; one being $IK_r$ the rapid rectifier and the second being $IK_s$, a slower ion channel in the human myocardium. While the anti-arrhythmic action of many agents on supraventricular arrhythmia and ventricular arrhythmias are moderated via inhibition of sodium channel (ex procainamide) the effect on the potassium channels ($IK_r$ and $IK_s$) may be an important anti-arrhythmic action. However, strong $IK_r$ blocking action often leads to pro-arrhythmia of the Torsade de Pointes variety. Thus, a chiral isolate that has less $IK_r$ action, but retains sodium channel inhibition may offer considerably less pro-arrhythmia. Additionally, an agent causing less contractile augmentation of the GI smooth muscle may also be a significant advantage, since so many patients discontinue quinidine due to the diarrhea. Contractile augmentation may not be the only mechanism of quinidine induced diarrhea. A secretory action of quinidine may also be an important contributor to the agents diarrheal effects.

Quinidine has a duplicate drug in nature, quinine, the well known anti-malarial agent. Quinine is the chemical mirror image of quinidine, similar to the differences of the right from the left hand—identical but can't overlap, a structural characteristic in chemistry known as chirality. This results in quinidine and quinine being stereoisomers of each other. Quinine not only causes constipation, rather than diarrhea, but it affects cardiac ion channels a lot less than quinidine. These differences come about because of the mirror image relationships of the molecule at one chiral center. Thus, because two different stereoisomers exist that have different configurations, they cannot fit into receptors the same way. Since it is assumed that the anti-arrhythmic action, QT prolongation, and diarrhea occur as a result of the molecules acting at specific receptor sites such as ion channels, it would be anticipated that they have differed effects at different ion channels. In fact, stereoisomeric segregation of drug effects is a well established pharmacological strategy to determine if a drug acts at a receptor site. Thus, if one stereoisomer is active and the other is not, this is taken to mean that the molecule acts at a specific binding site. The fact that quinidine and quinine are stereoisomers, but have different properties implies that the diarrhea and anti-arrhythmic effects of these drugs occur through different binding sites and different mechanisms.

However, what is not recognized previously is that there are three additional chiral centers on the molecule that then create a total of sixteen isomers. Besides the optically active site at carbon 2 (C-2) position that segregates quinidine from quinine, there are three additional sties at the C-3, C-15 and C-20 carbon positions. Considering all the possibilities, there are eight possible isomers that have quinidine conformation at the C-2 position. Likewise, quinine also has eight possible isomers, together with quinidine making a total of sixteen possible stereoisomers.

It is expected that the different stereoisomers of quinidine and quinine have differential biological effects. For example, individual stereoisomers of quinidine or quinine could have different and specific effects on cardiac potassium channels or cardiac sodium channels. In addition, individual stereoisomers of quinidine or quinine could cause increased GI motility.

The expectation of differential effects of stereoisomers of quinidine or quinine is supported by the many known examples of different stereoisomers compounds having significantly different biological activity. For example, the different stereoisomers of beta-blockers (e.g. levalbuterol, and beta-amino alcohols), amphetamine (AP), methamphetamine (MAP), and penicillamine have different pharmacological activities and pharmacokinetic behaviors. The S-isomers of AP and MAP are each approximately five times more active on the central nervous system (CNS) than their respective R-isomer.

The commercial success of stereoisomers with specific biological activities is demonstrated by the antihistamine terfenadine, the psychoactive agent fluoxetine and the pro-kinetic gastrointestinal agent cisapride. Terfenadine is originally sold as a racemate mixture of R- and S-isomers under the name Seldane®. After discovering that racemic terfenadine is preferentially oxidized in rats to form a carboxylic acid metabolite enriched in the R-enantiomer, Hoechst Marion Roussel began marketing the R-isomer of terfenadine as Allegra® (fexofenadine). A single isomer preparation of fluoxetine (Prozac) is under development and a single isomer version of Zyrtec (cetirizine) may be available in the near future. A single isomer version of cisapride is marketed as norcisapride, which has a different receptor binding profile than the parent racemic drug.

Preliminary data regarding the pharmacodynamics of stereoisomers, such as that mentioned above, suggest that individual isomers can possess significant differences in receptor-binding profiles and follow different courses of absorption, distribution, metabolism and excretion. As such, the administration of single isomers may significantly reduce if not eliminate drug interactions mediated by the effect of stereoisomers on different biological receptors. Similar to other racemic compounds, it is expected that individual stereoisomers of quinidine and quinine are responsible for the diversity of effects displayed by such compounds (e.g., action on cardiac sodium and potassium channels as well as effects on GI motility). The ability to identify isomers of quinidine and quinine with differential effects on cardiac sodium channels, cardiac potassium channels, and GI motility would offer considerable potential clinical benefits. For example, specific stereoisomers of quinine or quinidine could be used as drugs for blocking only cardiac sodium channels or blocking only cardiac potassium channels while not causing diarrhea. Alternatively, a stereoisomers of quinine or quinidine not effecting the cardiac sodium or potassium channels, but increasing GI motility or mucosal secretion could be used as novel treatment for constipation or Gastroesophageal reflux disease (GERD). Therefore, the isolation of specific stereoisomers of quinidine and quinine could lead to a safer, less toxic and less pro-arrhythmic compounds than racemic quinidine.

The present invention provides for the isolation of quinidine and quinine stereoisomers. The present invention also provides assays for quantitative determination of optically active isomers of quinine and quinidine in biological fluids. The present invention also provides for assays for measuring the effects of stereoisomers of quinidine and quinine on cardiac potassium and sodium channels, as well as contractility and secretory assays for determining GI motility activity.

SUMMARY OF THE INVENTION

The present invention provides methods for purifying, identifying and using optically active isomers of quinine and quinidine as well as compositions comprising such optically active isomers. Such optically active isomers having desired actions on cardiac sodium and potassium channel function substantially separable from undesirable effects on GI motility can be useful for more effective therapy of cardiac arrhythmias. Also disclosed are methods for assaying the levels of such isomers present in the biological fluids.

In general, the present invention relates to optically active isomers of quinine and quinidine and to methods of synthesis, isolation, purification, and systems using the same. The invention also relates to the use of optically active isomers of quinine and quinidine to specifically block cardiac sodium channels or cardiac potassium channels, as well as treating constipation or gastroesophageal reflux disease (GERD) by increasing gastrointestinal (GI) motility or by increasing luminal secretion or blocking luminal fluid re-absorption. The present invention also relates to methods of assaying the presence of optically active isomers of quinine and quinidine in biological fluids.

In another embodiment, the invention provides a stereoisomerically purified form of quinidine. A stereoisomerically purified form of quinidine is one that contains less than the eight possible stereoisomers (FIG. 2), in other words, from one to seven. In an even more preferred embodiment, this stereoisomerically purified form of quinidine has a less $I_{Kr}$ effect than commercial quinidine. In another more preferred embodiment, the stereoisomerically purified form has less illeal contractile augmentation than commercial quinidine.

In yet another embodiment, the invention provides a method of determining a therapeutic profile of a compound comprising the steps of contacting at least one first recombinantly expressed transmembrane ion channel with an effective amount of the compound and measuring the change in the function of the first recombinantly expressed transmembrane ion channel to determine a first index; contacting at least one second recombinantly expressed transmembrane ion channel with an effective amount of the compound and measuring the change in the function of the second recombinantly expressed transmembrane ion channel to determine a second index; contacting at least one gastrointestinal tissue sample with an effective amount of the compound and measuring the change in the function of the gastrointestinal tissue sample to determine a third index; and comparing the relative amplitudes of the first, second and third indices to determine the therapeutic profile of the compound. The function of an ion channel may be measured by means known in the art, such as electrical measurements, including measurements of current, conductance or charge displacement, or alternatively measures of ion flow, including using ion sensors or radioisotopes. In one embodiment, the first recombinantly expressed transmembrane ion channel is a sodium channel and the second recombinantly expressed transmembrane ion channel is a potassium channel. Alternatively, any suitable recombinantly expressed transmembrane ion channel may be used.

BRIEF DESCRIPTION OF THE DRAWINGS

The following detailed description, given by way of example, but not to limit the invention solely to the specific embodiments described, may best be understood in conjunction with the accompanying drawings, in which.

DETAILED DESCRIPTION OF THE INVENTION

Figure 1:
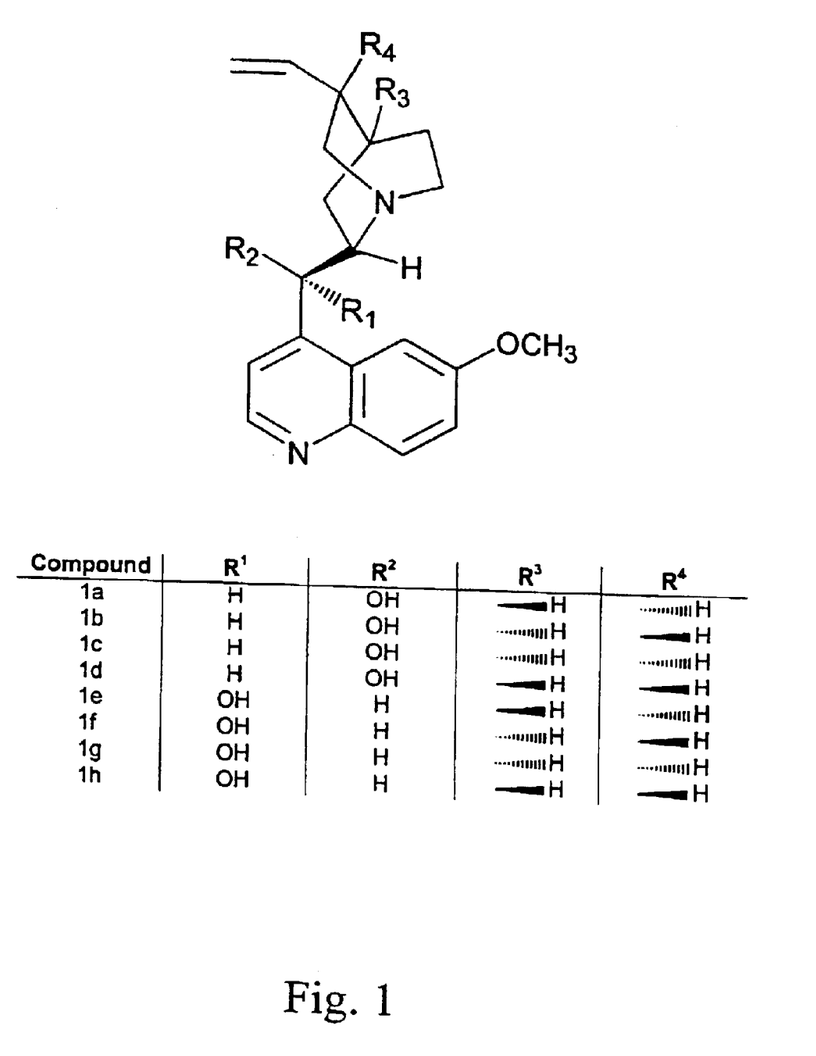
FIG. 1 shows the structure of quinine and the possible optically active isomers labeled 1 through 8.
Figure 2:
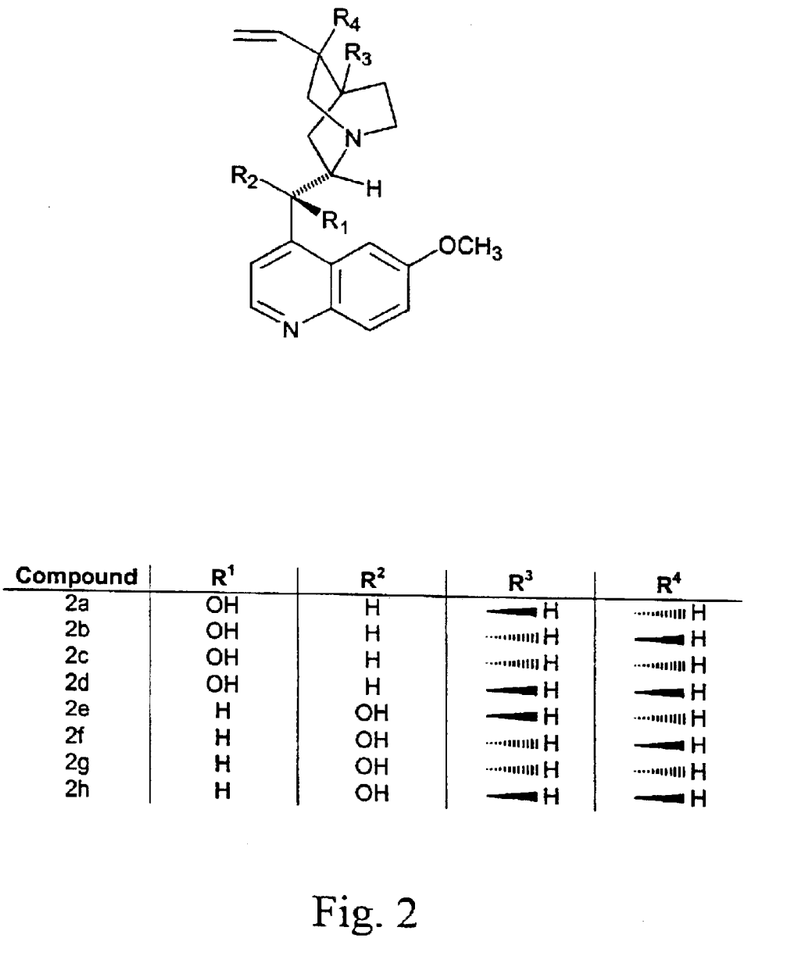
FIG. 2 shows the structure of quinidine and the possible optically active isomers labeled 1 through 8.

The present invention relates to the isolation of stereoisomers of quinine (FIG. 1) and quinidine (FIG. 2). The invention further relates to the following biological functions of each of the isomers: 1) action on cardiac potassium and sodium channels and increasing GI motility; 2) action on cardiac potassium channels and increasing GI motility; 3) action on cardiac sodium channels and increasing GI motility; 4) action on cardiac potassium and sodium channels, without increasing GI motility; and 5) increasing GI motility, without action on cardiac potassium and sodium channels.

In addition, the present invention relates to methods of isolating stereoisomers of quinidine and quinine using chiral columns in combination with high pressure liquid chromatography. Chiral columns have been used to effectively separate stereoisomers (Chan et al., *J. Chromatogr.* 1991, 571, 291–297). In addition, chiral columns can be used for determining enantiomeric purity.

Generally, resolution of stereoisomers of quinidine and quinine can be optimized through a combination of altering the composition of the mobile phase and altering the specific packing materials of the chiral columns. Separations are performed using non-polar organic phases (e.g. heptane, iso-octane, etc.) with polar organic additives, such as tetrahydrofuran, alcohols, chlorinated hydrocarbons or similar solvents with or without buffer such as phosphate or borate. Often, the addition of a small amount of a strong acid (e.g. trifluoroacetic acid) to the mobile phase will considerably improve separation of the isomers. Anion exchange chromatography with aqueous buffers using salt or pH gradients can also be used to effectively resolve enantiomers of quinidine and quinine.

The present invention also relates to isolating isomers of quinidine and quinine after selective epimerization of protons adjacent to the aromatic ring. Epimerization is usually accomplished by refluxing a solution of the isomers in an acidic medium. However, epimerization is not limited to this category of chemical reaction. Due to four chiral centers, quinine and quinidine have a total of sixteen stereoisomers, each of which can possess distinct pharmacological properties. However, some of the stereoisomers of quinidine or quinine may not readily occur due to the steric hindrance of the rigid bicyclo ring system which does not allow conformational flexibility (Karle I. L. et al., *Proc. Natl. Acad. Sci.* 1981, 78, 5938–5941; Karle J. M., *Antimicrob. Agents Chemother.* 1997, 41(4), 791–794).

The present invention also relates to assays to determine the electrophysiological activity of quinidine and quinine compounds by using voltage clamp techniques. In addition the present invention relates to assays to determine the biological activity of quinidine and quinine compounds by performing GI motility studies.

The human heart $Na^+$ channel $SCN_5A$ construct encodes the Ina (sodium channel) current which is antagonized by class I anti-arrhythmic drugs. Voltage-gated $NA^+$ channels are essential for normal electrical excitability and are responsible for the rapid membrane depolarization that characterize the initial phase of the action potential in most excitable cells (Catterall W. A., *Physiol. Rev.* 1992, 72 (4 supp.): S15–48). In myocardium, $Na^+$ channel activates rapidly upon depolarization and the fast inactivation contributes to the control of membrane refractoriness during repetitive stimulation and is an important determinant of class I antiarrhythmic drug action (Vaughn Williams E. M. et al., "Class I Anti-arrhythmic Action, chapter 2"; *In Control of Cardiac Rhythm,* Lippincott-Raven Publishers, New York 1998). Demonstrating dose-dependent antagonism of this channel would therefore identify a compound as belonging to the Class Ia antiarrhythmics of which quinidine is the prototypical agent.

The human heart $Na^+$ channel clone hHla, which is an expression plasmid of the $SCN_5A$ gene, has been previously described (Kraft D. S. et al., *Molecular Pharma.* 1994, 266, 245–254). In brief, the full-length cDNA is cloned into the pGM3 plasmid vector (Promega). The corresponding cRNA can be injected into *Xenopus* oocytes whereby the ion channel proteins are expressed and localized to the cell membrane surface. The ionic flux through the expressed cardiac sodium or potassium channels can then be measured. This new technology offers the opportunity to study the effects of stereoisomers obtained through chiral separation on a defined population of ion channels.

The human ether a-go-go-related gene (HERG) encodes a protein which assembles to form a transmembrane ion channel. The resulting currents after the expression of the HERG gene in *Xenopus* oocytes indicate that the HERG gene encodes a potassium channel with biophysical properties identical to the rapid component of the cardiac delayed rectifier, $I_{Kr}$ (Sanguinetti et al., *Cell* 1995, 81, 299–307). It is postulated that in humans $I_{Kr}$ is a critical component in the repolarization process of the myocardium (Li et al., *Circ. Res.* 1996, 78, 689–696). The $I_{Kr}$ current is selectively blocked with high affinity by methanosulfonalides, such as E-4031, ibutilide, and dofetilide (Sanguinetti et al., *J. Gen. Physiol.*, 1990, 96, 195–215). The biophysical properties of the protein encoded by the HERG gene indicate the gene codes for the cardiac delayed rectifier protein (Trudeau et al., *Science* 1995, 269, 92–95; Spector et al., *J. Gen. Physiol.* 1996, 107, 611–619; Kiehn et al., *Circulation* 1996, 94, 2572–2579; Ficker et al., *Circ. Res.* 1998, 82, 386–395).

The slow component of the cardiac delayed rectifier ($I_{Ks}$) modulates the repolarization of the human cardiac action potential (Li et al., *Circ. Res.* 1996, 78, 689–696). The proteins encoded by the KVLQTI and hminK (KCNEI) genes co-assemble to form $I_{Ks}$ (Sanguinetti et al., *Nature* 1996, 384, 80–83; Barhanin et al., *Nature* 1996, 78–80). The $I_{Ks}$ protein is a target for class III antiarrhythmics (Busch et al., *Eur. J Pharmacol.* 1994, 264, 33–37). The $K^+$ currents can also be blocked by quinidine, a class I antiarrhythmic agent that also has class III action predominately blocks the rapid $K^+$ current $I_{Kr}$. (Synders et al., *Mol. Pharmacol.* 1991, 41, 322–330).

The $SCN_5A$ gene encodes $I_{Na}$, which are voltage-gated sodium channels essential for normal electrical excitability. $I_{Na}$ is responsible for the rapid membrane depolarization that characterize the initial phase of the action potential in most excitable cells. In myocardium, the voltage-gated sodium channels activate rapidly upon depolarization and contribute to the control of membrane refractoriness during repetitive stimulation. Defects in the fast component of the inactivation of cardiac sodium channels are responsible for idiopathic ventricular fibrillation syndrome (Chen et al., *Nature* 1998, 392, 293–296). As compared to the fast component, defects in the slow component of the inactivation of sodium channels are responsible for the LQT3 form of long QT syndrome (Wang et al., *Hum. Mol. Genet.* 1995, 4, 1603–1607; Bennet et al., *Nature* 1995, 376, 683–685). Furthermore, the $I_{Na}$ current is a target for class I antiarrhythmics.

Figure 3:
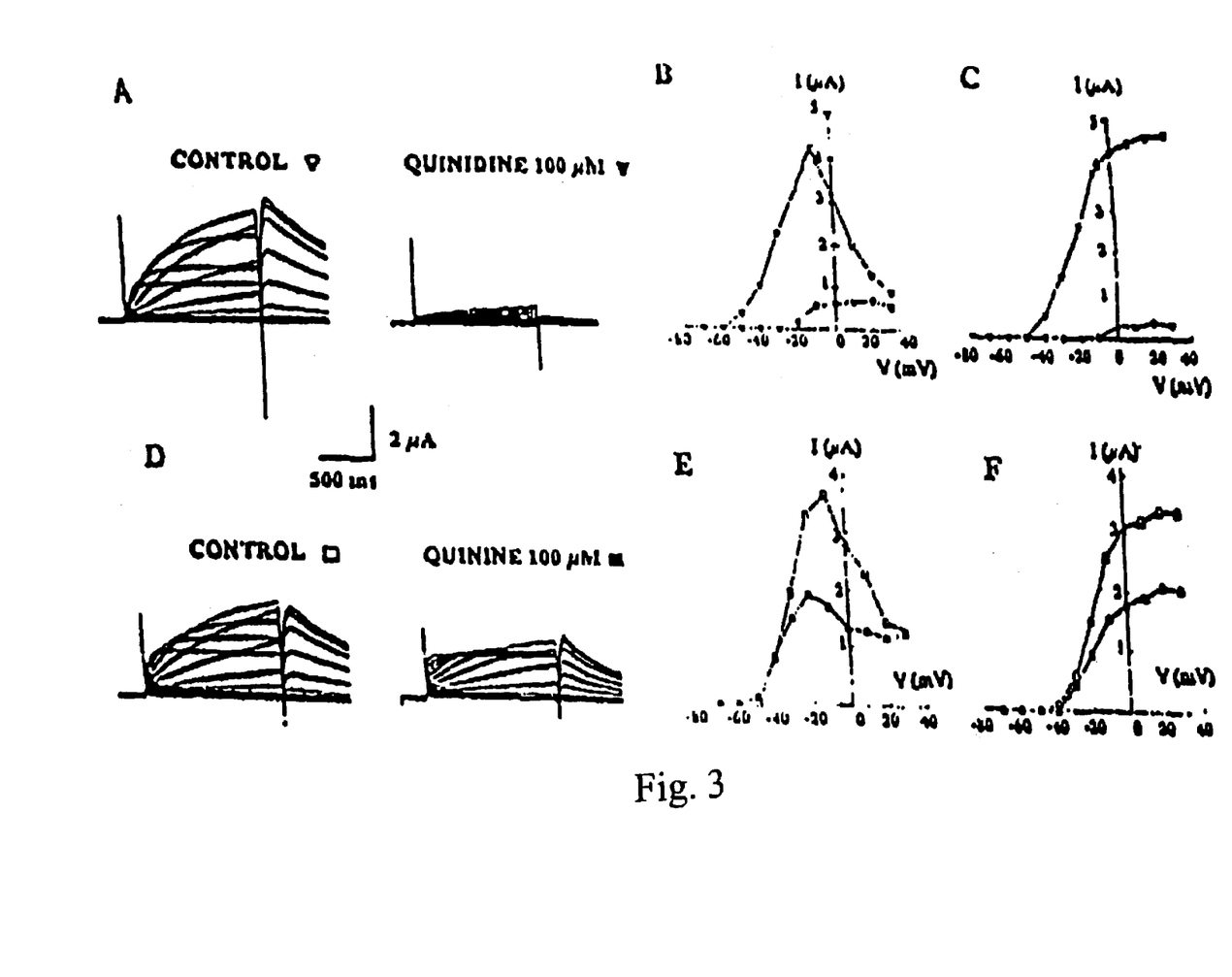
FIG. 3 shows the effect of quinidine and quinine on the potassium channel ($IK_r$) measured in *Xenopus* oocytes. Control current is obtained after 4 min. of stimulation pulse from −80 mV to 0 mV at 1200 ms (panel A). Quinidine 100 $\mu$M significantly inhibits the $IK_r$ current. Panel B shows an IV plot of the peak current before and after quinidine and panel C shows the tail current IV plot. Panels D, E and F show the much reduced action of quinine on $IK_r$. These results are consistent with the clinical observation that quinidine prolongs the QT interval, while quinine usually does not.

Quinidine and quinine have been evaluated in the frog oocyte model. Studies reveal markedly different effects on potassium and sodium channels. Studies utilizing 100 $\mu$M quinidine reveal marked inhibition of the potassium channel while 100 $\mu$M quinine had only minimal effects (FIG. 3). Since it is likely that $K^+$ channels play a potential role in the induction of diarrhea, the failure of quinine to affect these channels is consistent with its GI effect of causing constipation. Moreover, since quinine has no pro-arrhythmic action thought to be associated with the $K^+$ channel ($IK_r$) effect, the profile observed in this model with quinine is predictive of the clinical effects of this drug.

In yet another embodiment, the stereoisomerically purified compound of the present invention can be used as safer anti-arrhythmic and safer anti-malarial agent than either quinine or quinidine.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

EXAMPLE 1

Purification of Quinidine. Quinidine is known to contain up to 20% dihydroquinidine as an impurity. In order to obtain pure quinidine (>99%) and avoid interference due to this impurity, commercial quinidine (containing dihydroquinidine) is subjected to purification using HPLC. The HPLC procedure utilizes a $C_{18}$ $\mu$-Bondapak column operated isocratically with 0.05 M sodium (or potassium) phosphate buffer (pH 3.0) and acetonitrite (73:27, v/v) at a constant flow-rate of 1 ml/min. The UV variable wavelength detector is set at 237 nm and the liquid chromatograph employed is a Spectral Physics Apparatus. Portions of the eluent containing the quinidine (as indicated in the chromatogram) are collected, concentrated and later subjected to HPLC analysis. Following separation, this analysis indicates the quinidine peak to be greater than 99.9% pure.

Chromatographic Isolation of Quinine and Quinidine Isomers. Chiral separation is performed using a Spectra-Physics HPLC instrument and UV variable wavelength detector set at 254 nm. The chromatographic column is a pre-packed 25 mm×4.6 mm ID Cyclobond I (5 $\mu$m) operated with a methanol—0.014 M sodium perchlorate (75:25 v/v) mobile phase, at a flow rate of 0.2 ml/min. Alternatively, a pre-packed 150 mm×4 mm ID Resolvosil BSA-7 column (5 $\mu$m) may be operated isocratically with 0.05 M sodium phosphate buffer (pH 3.0)—acetonitrile (73:27 v/v) at a flow rate of 0.2 ml/min.

The identification of each isomer of quinidine and quinine can be made using a combination of 2- or 3-dimensional high resolution NMR ($^{13}C$ and proton) spectroscopy using a chiral shift reagent, mass spectrometry, and optical activity. In order to obtain isomers of quinidine and quinine having the desired optical purity, eluted samples may need to be rechromatographed.

Figure 4:
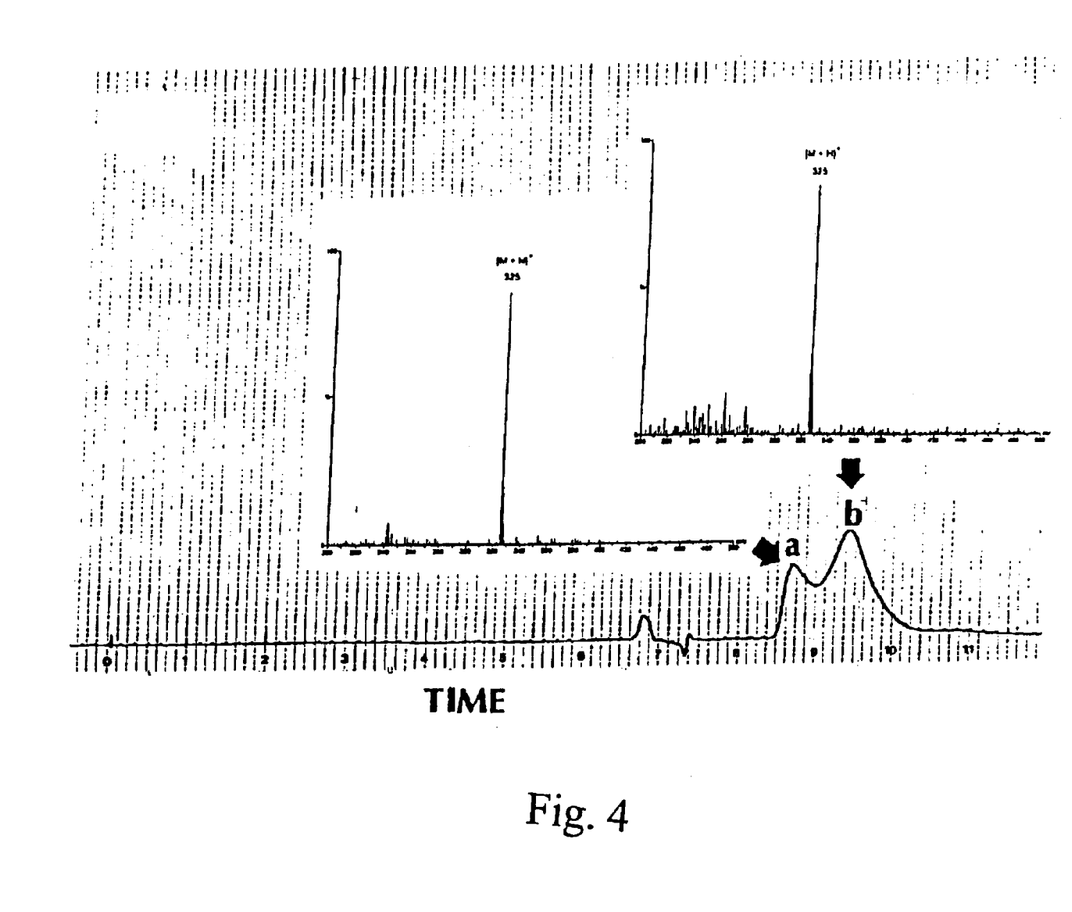
FIG. 4 shows a chiral HPLC chromatogram of two peaks, a and b. The insert is the mass spectrum which indicates the molecular weight of each isomer to be 325, corresponding to that of quinidine for each of the two peaks. Thus, the two peaks are both quinidines, but stereoisomers.
Figure 5:
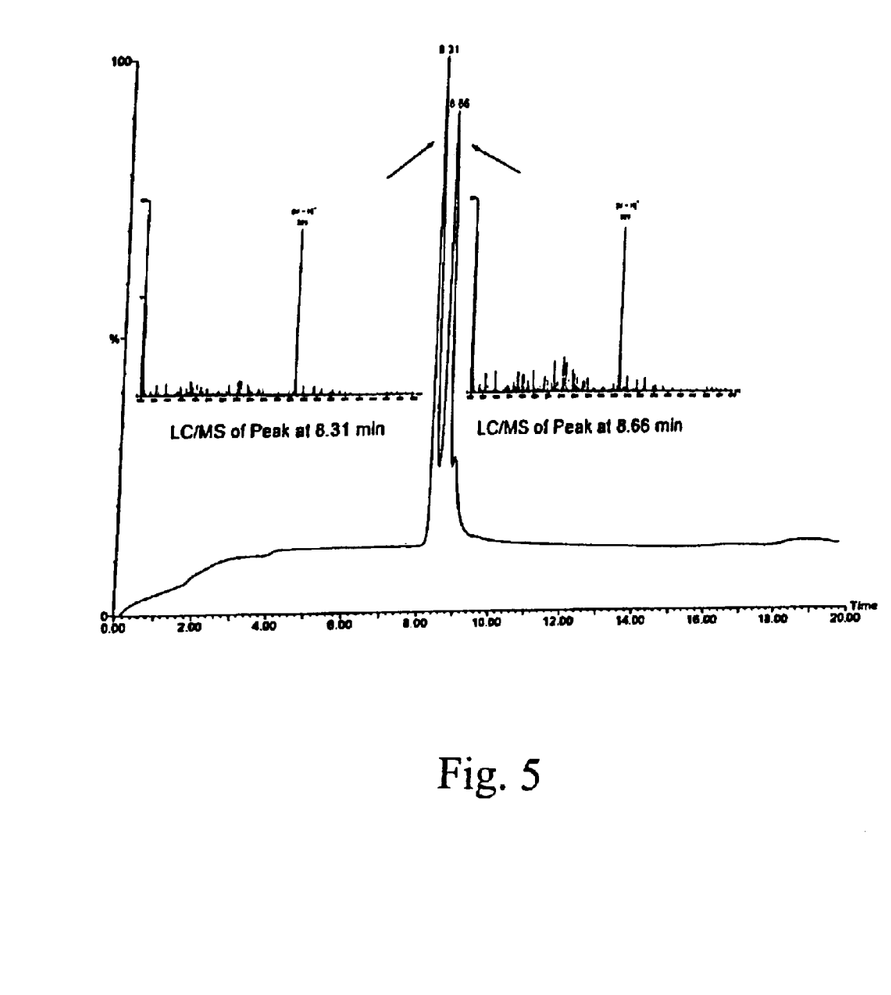
FIG. 5 shows a chiral chromatogram of LC-MS of two peaks, having retention times of 8.31 and 8.66 min., respectively. The insert is the mass spectrum of two peaks. Mass spectrum indicates molecular weight of 325, corresponding to that of quinidine for each of the two peaks. Thus, the LC separated the two isomers (or mixture of isomers) of quinidine.

Chiral Separation of Quinidine. Chiral separation is performed using a Spectra-Physics HPLC instrument and UV variable wavelength detector set at 254 nm. The chromatographic column is a pre-packed 250×4.6 mm ID Cyclobond I ($\beta$-cyclodextrin; 5 $\mu$m spherical particles; Alltech Inc.). The mobile phase is $CH_3CN$ (or methanol): $NH_4$-acetate (0.05 m) buffer (27:73) (v/v), pH adjusted to 3.5 and the instrument is operated isocratically with a flow rate of 1.0 ml/min. The HPLC analysis results in two peaks in the chromatogram with retention times of 5.6 min and 5.9 min for peak a and peak b, respectively (FIG. 4). Eluents are collected at their respective retention times. Mass spectral analysis (using Micromass-Waters LC-MS #1690 spectrometer) of the aliquots containing both fractions indicate a molecular weight of 325.4 (FIG. 4), which confirms the presence of quinidine isomer(s) in each of the two fractions. The concentration of each fraction is determined from the UV absorbances compared to those of the known concentrations of quinidine reference samples. The results indicate that each fraction has a concentration of 1.4 mM/L. Chiral chromatograms of LC-MS of the two isolated peaks having retention times of 8.31 and 8.66 min. are obtained. Both peaks have a mass spectral analysis indicating a molecular weight of 325 corresponding to quinidine (FIG. 5).

Optical rotations of these isomer fractions are determined using a Perkin-Elmer Polarimeter and the following formula:

$$^{20}[\alpha]_D = \frac{100\,\alpha}{C}$$

Where, C=1.4 mMole/L or 0.053 gm/100 ml
α=Polarimeter Reading
Therefore for peak a, $$[\alpha]_D^{20} = \frac{100 \times O}{0.053} = \pm O°$$

For peak b, $$[\alpha]_D^{20} = \frac{100 \times O\,0.115}{0.053} = +217°$$

The above optical rotation data demonstrates at least partial purification of the various stereoisomers. However, it is likely that peaks a and b do not each contain a single isomer. Thus, these two isolated fractions may still contain a mixture of isomers probably in uneven proportions.

EXAMPLE 2

Assay for Isomers of Quinine and Quinidine. The following methods are available and routinely used for assaying quinine and quinidine in biological fluids: 1) high-pressure liquid chromatography using normal or reverse phase columns ($C_8$ or $C_{18}$) and isocratic or gradient solvent systems and either fluorescence or UV detector (Carignan et al., 1995; Ahokas et al., 1980); 2) solid-phase extraction following by HPLC; 3) enzyme multiplied immunoassay (EMIT); 4) radioimmunoassay followed by HPLC; and 5) fluorescence polarization immunoassay (FPIA) with HPLC.

Examples of Type 1 use a chiral stationary phase (e.g., Resolvosil) in order to achieve enantiomeric separation of the isomeric compounds of quinine and quinidine. The liquid chromatograph (Spectra Physics) is equipped with a Resolvosil column protected by a Suplex pkb-100 guard column 20×4.6 mm ID 5 μm particle size and UV variable wavelength detector set at 237 nm. The mobile phase consists of a mixture of aqueous $H_2SO_4$ solution (0.01 M, pH 2) methanol-acetonitrile (45:45:10) containing 10 mM octanesulfonic acid sodium salt and is filtered through a 0.2 μm Ultipor $N_{66}$ membrane.

1. Sample Preparation

To a 1.0-ml aliquot of plasma is added 200 μl of the working standard containing only the internal standard and 1.0 ml of aqueous $K_2HPO_4$ (0.2 M, adjusted to pH 10 with 5 M KOH). The solution is briefly mixed and then 5 ml of methyl tert-butyl ether is then added. The tube is capped and vigorously shaken for 10 min, then centrifuged for 10 min at 2500 g. A 4-ml aliquot of the upper organic phase is transferred to another tube and evaporated to dryness using a vortex evaporator at 30° C. 2 ml of freshly purified hexane and 200 μl of reconstituting solvent are added, and the tube is vortexed for 2 min. Most of the upper hexane layer is discarded. The aqueous phase is washed a second time with 2 ml of purified hexane. The aqueous phase is transferred into an autosampler vial, and a 100 μl aliquot is chromatographed.

2. Standard Curve Preparation

Concentrations of quinidine and quinine isomers in samples are calculated by using a standard curve generated by regression analysis. Standard curve samples are prepared by spiking 1 ml of blank plasma with 200 μl of working standard solutions containing isomers of quinine and quinidine and internal standard samples. The standard curve is generated using the linear least-squares regression equation to fit the ratios of peak height of isomers of quinine and quinidine to the internal standards against concentrations using a weighting correction factor of 1/concentration$^2$.

The internal standard is 4-diisopropyl-amino-2p-chlorophenyl-2(2-pyridyl)-butyramide or 4-methyl propranolol HCl. The chromatography column and system are the same as above. The solvent system is used isocratically with 0.05 M sodium phosphate buffer (pH 3.0)—acetonitrile (73:27 v/v), at a constant flow-rate of 0.2 ml/min. The sample may be prepared using the same as described above.

EXAMPLE 3

Na Channel expression and characterization. The $SCN_5A$ gene encoding the human cardiac sodium channel is derived from the hH1A expression plasmid (Gellens et al., Proc. Natl. Acad. Sci. 1992, 89, 554–558; Hartmann et al., Circ. Res. 1994, 75, 114–122). The full-length cDNA is cloned into the pGEM3 plasmid vector (Promega). The DNA construct is linearized by digestion with HindIII for runoff transcription. In vitro transcription with T7 RNA polymerase is performed using the Message Machine kit (Ambion). The amount of cRNA synthesized is quantified by the incorporation of trace amounts of [$^{32}P$]UTP (phospho uracil three phosphate) in the synthesis mixture. The final cRNA product is then suspended in 0.1 mM KCl at 200 μg/μl and stored at −80° C. The cRNA is diluted to a concentration of about 10 pg/nl before oocyte injection. Expression of $SCN_5A$ currents in Xenopus oocytes is obtained after cRNA injection of the corresponding genes.

Figure 6:
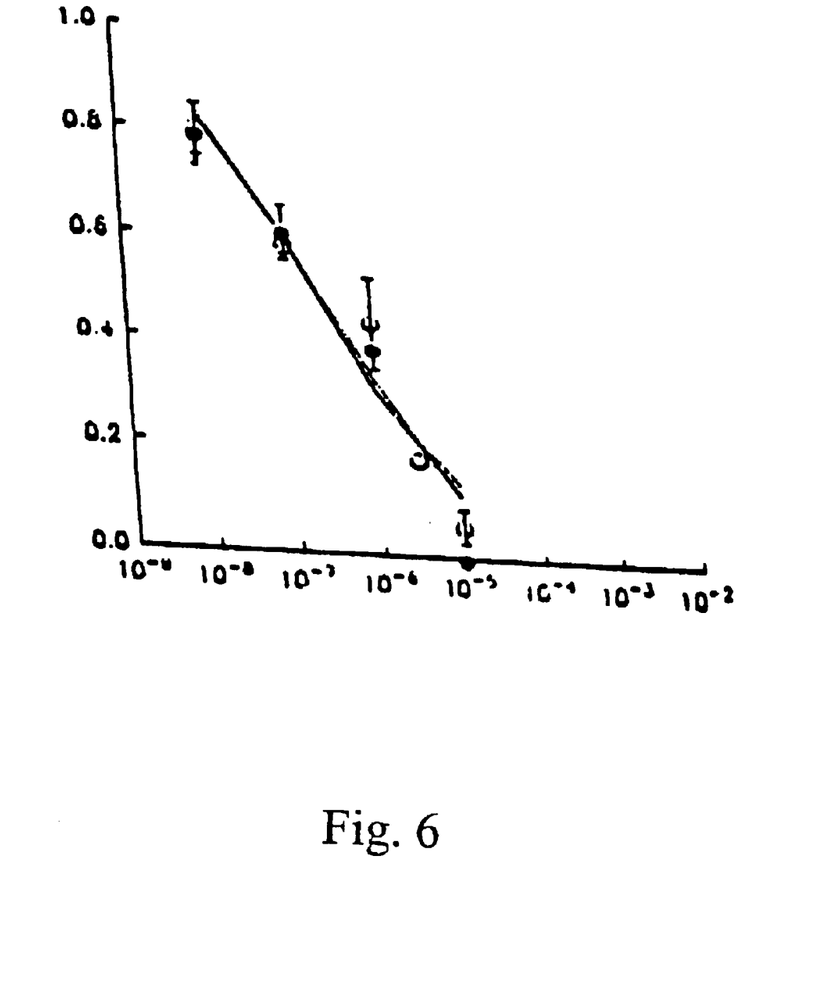
FIG. 6 depicts the effect of the two chirally separated peaks of quinidine on sodium channel inhibition at various concentrations.

For $SCN_5A$ currents the following protocol is used: a) I-V plot, oocytes are kept at a holding potential of −80 mV, then step pulsed from −70 mV to +30 mV in 10 mV increments of 40 ms are applied returning to −80 mV. b) Single pulses, from a holding potential of −80 mV are used. Then continuous perfusion of the drug is given over two minutes and the cell is stimulated with a pulse from −80 mV to −10 mV during 25 mins at a frequency of 0.3 Hz. After 4 minutes the peak current is measured at −10 mV. Currents are recorded with the conventional two micro-electrode voltage clamp technique in a bath solution containing in mM: NaCl 96, KCl 2, $CaCl$ 1.8, $MgCl$ 1.0 and HEPES 5, at a pH 7.4. Using these techniques the two chirally separated peaks of quinidine demonstrated very similar properties (FIG. 6).

The results show that both peaks a and b have almost identical dose related effects on sodium channel inhibition. Thus, both chirally distinct products have a critical antiarrhythmic activity, i.e. inhibition of the sodium channel, a fundamental property of Vaughan Williams class I action. It is important to note that sodium channel inhibition does not cause QT prolongation or Torsade de Pointes ventricular tachycardia.

EXAMPLE 4

Construction of HERG expression plasmid and cRNA transcription. The HERG gene encoding cardiac potassium channels is similarly derived from the pgH19 construct (Trudeau et al., 1995). For cRNA injection into Xenopus oocytes, the DNA is linearized by NOT1 and in vitro transcription is conducted with T7 RNA polymerase using the Message Machine kit (Ambion).

EXAMPLE 5

Potassium Channel Expression and Characterization

1. $I_{Kr}$

Wild type human minK (KCNE1) and KVLQT1 cDNA are isolated from human cardiac and pancreas cDNA libraries and cloned into the pSP64 poly (A) vector (Promega). For transcription in oocytes, the minK is subcloned from genomic DNA using the MKEL and MKER primers. The final minK expression construct contains cDNA inserted in the plasmid vector (PROMEGA). For the injection into *Xenopus* oocytes, cRNA is prepared using the mCAP RNA capping kit (Stratagene) following linearization of the expression construct by restriction digestion with EcoRI for run-off transcription.

In-vitro transcription is performed with SP6 RNA polymerize using the mMessage Machine kit (Ambion). The final capped-cRNA product is resuspended in 0.1 mM KCL and stored at $-80°$ C. The concentration of synthesized RNA is estimated by separating the denatured cRNA on a 1.5% agarose gel together with the 0.24–9.5 kb RNA ladder (Gibco-BRL).

HERG currents expressed in *Xenopus* oocytes are obtained using conventional two micro-electrode voltage clamp technique in a solution containing in mM: NaCl-96; KCl-5; CaCl-1.8; MgCl-1.0; and HEPES-5, at a pH of 7.4. The currents shown have nearly identical biophysical properties to the rapid component of the cardiac delayed rectifier current, $I_{Kr}$. From a holding potential of $-80$ mV, HERG currents are activated at potentials positive to $-50$ mV and have a peak current value at 0 mV. At more positive potentials, the magnitude of the current progressively decreases.

Using these methods, recordings are obtained in which peak a of the chiral isolation has a minimal inhibitory effect on the potassium channel while peak b has a marked effect in inhibiting $I_{Kr}$. Inhibition of $I_{Kr}$ will lead to an increase in APD duration and thus QT prolongation (peak b).

Figure 7:
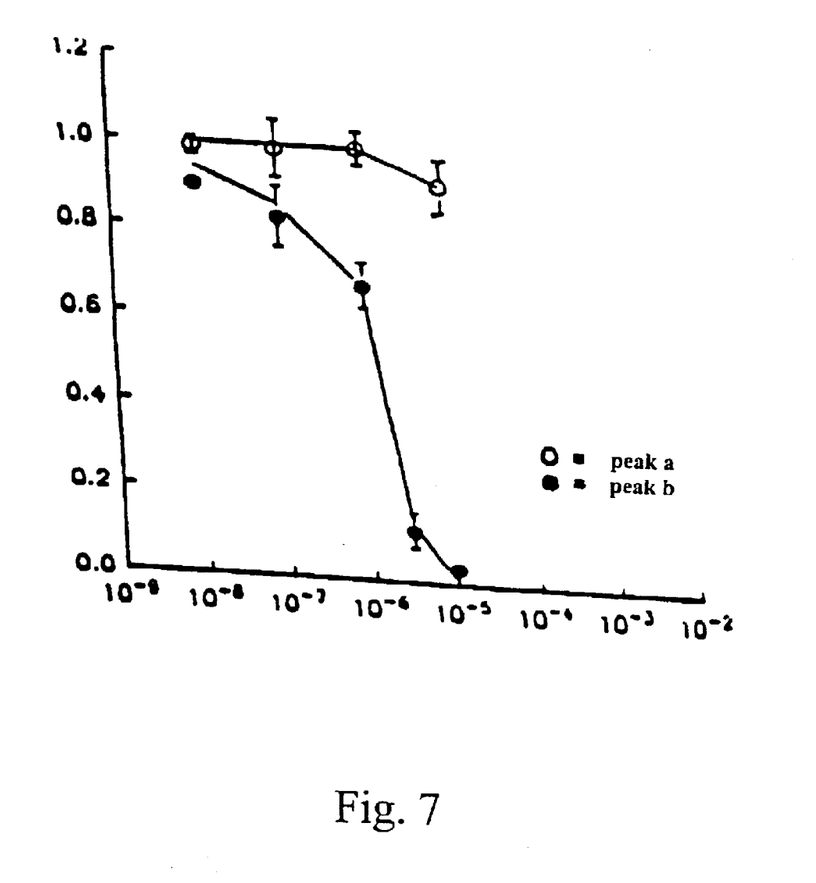
FIG. 7 The effect of the two eluent peaks on the potassium channel ($IK_r$) measured in xenophions oocytes. Peak b shows inhibition similar to a concentration effect relationship as seen with quinidine. Peak a has a minimal effect.

Since peak a has sodium channel inhibitory activity and no potassium channel inhibitory activity, peak a has anti-arrhythmic activity while not having the potential pro-arrhythmic action associated with QT prolongation. The preliminary data shows that the two chiral eluents have two very different properties. One being the typical quinidine effecting INa and $IK_r$ (peak b) while the other is a sodium channel blocker similar to procainamide in cellular anti-arrhythmic action.(peak a) (FIG. 7).

2. $I_{Ks}$ (For Quinidine only, not for Peak a or b)

Wild type human minK (KCNE1) and KVLQT1 cDNA are isolated from human cardiac and pancreas cDNA libraries and cloned into the pSP64 poly (A) vector (Promega). For transcription in oocytes, the minK is subcloned from genomic DNA using the MKEL and MKER primers. The final minK expression construct contains cDNA inserted in the plasmid vector (PROMEGA). For the injection into *Xenopus* oocytes, cRNA is prepared using the mCAP RNA capping kit (Stratagene) following linearization of the expression construct by restriction digestion with EcoRI for run-off transcription.

In-vitro transcription is performed with SP6 RNA polymerize using the mMessage Machine kit (Ambion). The final capped-cRNA product is resuspended in 0.1 mM KCL and stored at $-80°$ C. The concentration of synthesized RNA is estimated by separating the denatured cRNA on a 1.5% agarose gel together with the 0.24–9.5 kb RNA ladder (Gibco-BRL).

KVLQT1+KCNE1 currents are recorded with a solution containing in mmol-L: NaCl-96; KCl-2 $CaCl_{2-1.8}$; $MgCl_{2-1.0}$; and HEPES 5, pH 7.4. The following testing protocols are used: a) I-V plot, oocytes are held at $-80$ mV, then step pulses from $-60$ mV to $+40$ mV in 20 mV increments of 18 seconds are applied returning to $-40$ mV; b) Single pulses, the same protocol is applied for control current and after drug perfusion for current measurement. From a holding potential of $-80$ mV to a test potential of $+40$ mV during 18 seconds a pulse is applied. Quinidine is then infused continuously at a rate of 2 ml/min. over two to four minutes. The cell is either left at a resting potential of $-80$ mV or stimulated from a holding potential of $-80$ mV to a test potential of $+40$ mV during 1000 ms in a frequency range of 0.3 Hz.

Figure 8:
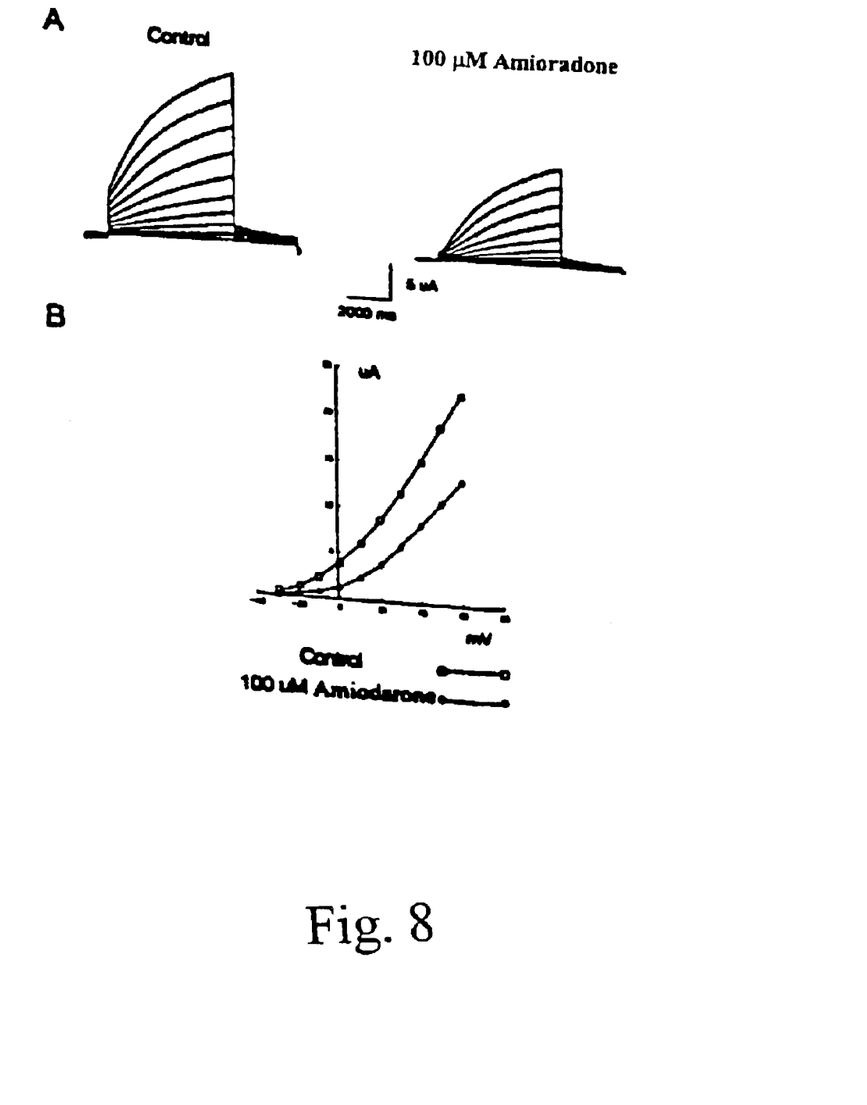
FIG. 8 shows the effect of amiodarone on $IK_s$. Panel A shows that 100 $\mu$M amiodarone inhibits the current flow across the $IK_s$ channel in xenophas oocytes. Panel B shows that at any voltage current ($\mu$A) through the $IK_s$ channel is reduced when 100 $\mu$M amiodarone is present.

The effect of different concentrations of quinidine on the $I_{Ks}$ currents are evaluated at concentrations of quinidine from $10^{-6}$ to $10^{-4}$ with a 14 to 52% reduction, respectively (see Table 1 below). This inhibition of $I_{Ks}$ is similar to that seen with amiodarone (FIG. 8) and is less than the inhibition seen on $I_{Kr}$ across the concentrations studied.

TABLE 1

| CONCENTRATION (Molar) | AMIODARONE (% of block) | QUINIDINE (% of block) |
|---|---|---|
| $10^{-6}$ | 15 ± 1 | 14 ± 5 |
| $10^{-5}$ | 30 ± 3 | 21 ± 7 |
| $10^{-4}$ | 47 ± 1 | 52 ± 5 |

EXAMPLE 6

Isolation of oocytes and cRNA injection. *Xenopus laevis* frogs are anesthetized by immersion in 0.2% Trocaine for 15–30 min. A small incision is made in the lateral ventral quadrant of the abdomen and a small piece of ovarian tissue is removed. The incision is then sutured at both the muscle and the cutaneous layers with fine silk thread and the animal is allowed to recover. The ovarian lobe is digested with 10 mg/ml type 1A collagenase (Sigma) in calcium-free solution for 30–60 min to remove the follicle layer. Stage V and VI oocytes are injected with 40 nl of a solution containing 10 to 50 ng/µl cRNA of either SCN5A, HERG, or hminK and KVLQT1, and then incubated at 19° C. in a modified bath solution for 2–8 days.

EXAMPLE 7

Rat Ileum Studies and Characterization of Chiral Separation Products. Guinea pig ileum is harvested and placed in warm (37° C.) Krebs Hanselest buffer and oxygenated (95% $O_2$ and 5% $CO_2$). Segments approximately 4.5 cm long are placed on a transducer (Gilson Instruments) and a preload of 1 gm is placed on the tissue. The tissue is then placed in a chamber and bathed in Tyrode's solution (37.5° C.) and oxygenated (95% $O_2$ and 5% $CO_2$). Muscle contractions are measured isometrically. After stable contractions are obtained, a study compound is added to the tissue bath and recordings are made until a new steady state of contraction is obtained. Following a washout period, a new steady state of contraction is recorded and then the procedure repeated with a second dose of the drug being evaluated. Changes in contraction magnitude are recorded as the percentage change from baseline. This procedure is a modification of the technique described by Van Neuten and associates (Van Neuten et al., *Life Sci.* 1978 28:453–458). Table 2 depicts the effects of quinidine and its derivative chiral products (peaks a and b) on ileum strip contractility.

TABLE 2

|  | Baseline | $10^{-7}$ M | $10^{-6}$ M | $10^{-5}$ M |
|---|---|---|---|---|
| Quinidine |  |  |  |  |
| Slow waves | 2.5 ± 0.5* | 3.3 ± 0.6 | 3.0 ± 0.5 | 6 ± 1 |
| Bursts | 8 ± 2 | 8 ± 2 | 7.7 ± 1.2 | 14 ± 4 |
| Spikes | 10 ± 1 | 11 ± 1 | 13 ± 2 | 15 ± 1 |
| Peak a |  |  |  |  |
| Slow waves | 2 ± 0 | 2.5 ± 1 | 2.3 ± 0.7 | 2.3 ± 0.6 |
| Bursts | 4 ± 0 | 5.7 ± 2 | 6.2 ± 1 | 4.8 ± 1 |
| Spikes | 11 ± 0 | 10 ± 5 | 9 ± 3 | 10 ± 4 |
| Peak b |  |  |  |  |
| Slow waves | 2 ± 0 | 2.5 ± 0.5 | 3.2 ± 0.3 | 4.3 ± 0.6 |
| Bursts | 4.7 ± 4 | 7.5 ± 0.9 | 13 ± 2 | 20 ± 3 |
| Spikes | 10 ± 2.6 | 19 ± 4 | 23 ± 4 | 11 ± 3 |

*mean ± standard deviation

The preparation permits the identification of slow waves of contraction, bursts of contraction of the smooth muscle and spikes of marked cross-sectional contraction. Each of the measures can be used as a measurement of contractile effect of an agent. Table 2 above shows that quinidine in a dose response fashion causes an augmentation of slow wave contractility, burst contractility and spike contractility. Peak a has minimal effect on slow waves and spikes, and an inconsistent and non-significant effect on burst frequency. Peak b behaves in an analogous fashion to quinidine with an increase in all three measures.

Figure 9:
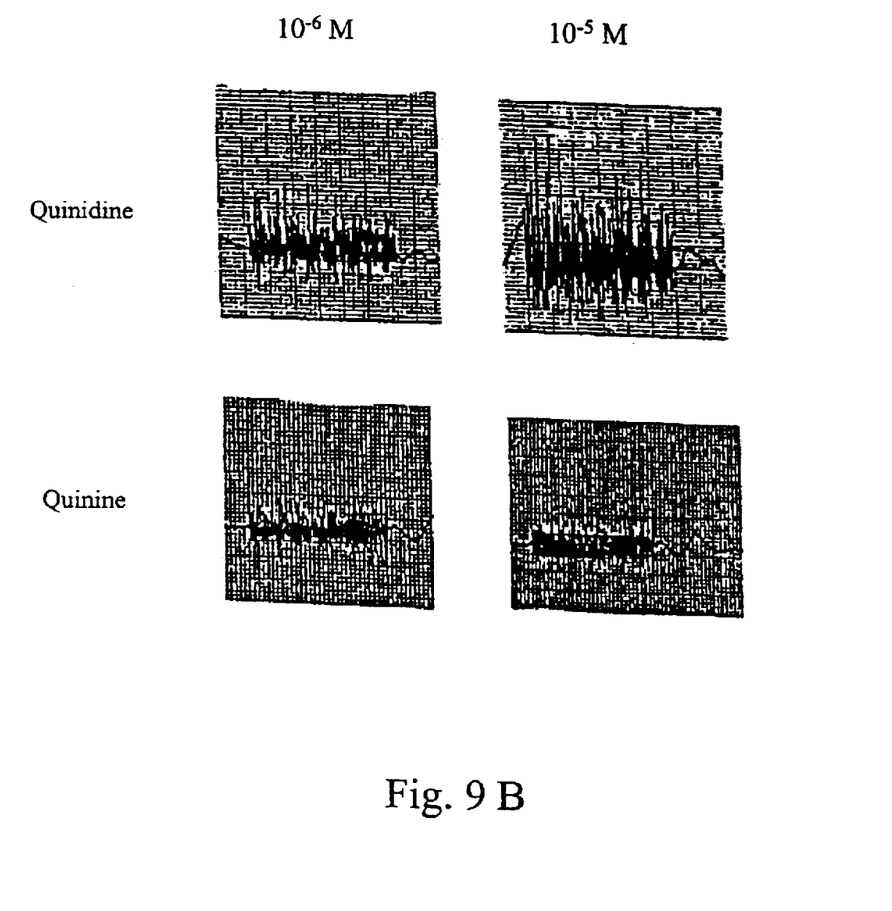
FIG. 9 represents tracings before and after quinine and quinidine is exposed to a rat illeal strip preparation. Quinidine at $10^{-7}$ and $10^{-6}$M (but not quinine) reduces the magnitude of contraction (trace amplitude) as well as reducing spikes (tall pen deflections). These tracings conform to the clinical observation that quinidine increase GI motility, while quinine does not.
Figure 9A:
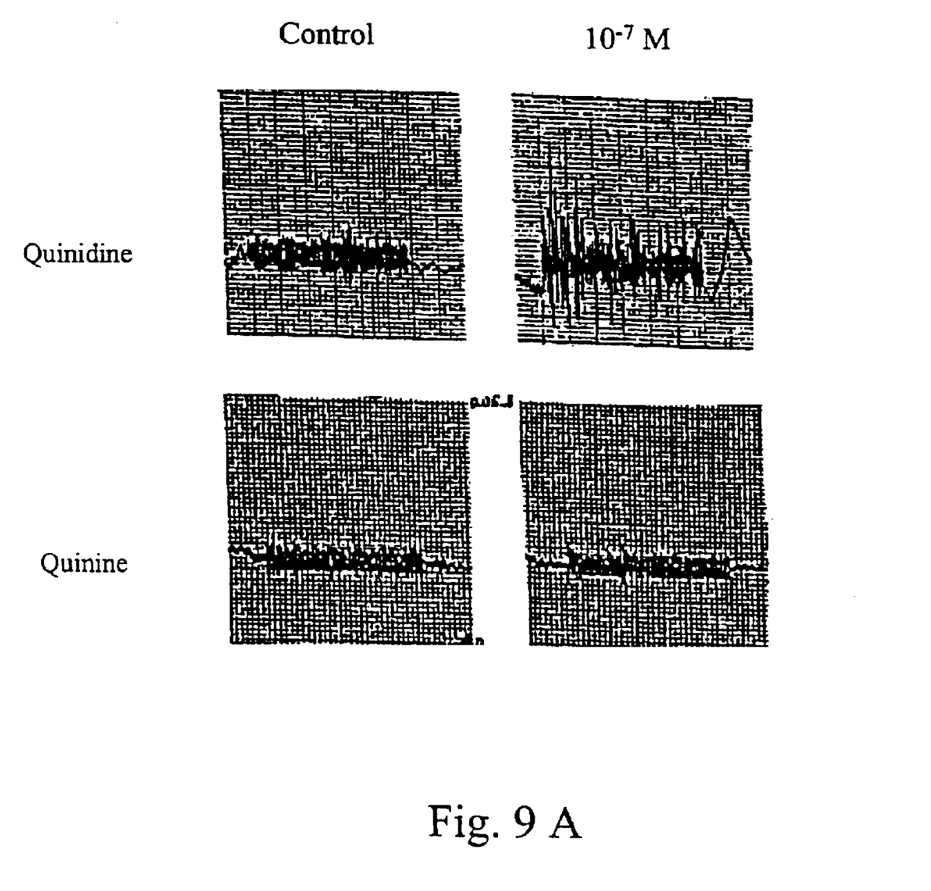

A graphic representation of the effect of quinidine and quinine is represented in FIG. 9. While quinidine at $10^{-7}$ M and $10^{-5}$ M increases slow waves (magnitude of pen deflection) and spikes (thin lines shooting up), quinine has no effect.

EXAMPLE 8

Differential Effects of Quinidine and Quinine on $I_{Kr}$. Electrophysiological studies are performed on cardiac potassium channels using quinidine (D-isomer) and quinine (L-isomer). $I_{Kr}$ currents are obtained by injection of cRNA from the HERG gene into *Xenopus* oocytes as described above. Recordings are made with an external [K$^+$] of 5 mM, −80 mV of holding potential and test potentials of 1200 msec in steps of 10 mV from −50 to +40 mV. The peak current is measured at 30 mV. The effects of quinidine and of quinine are determined at concentrations of $10^{-6}$, $10^{-5}$, and $10^{-4}$ M.

The IC$_{50}$ for $I_{Kr}$ block is 6.4±1.9 μM for quinidine and 80.2±2.1 μM for quinine. At 0.33 Hz stimulation frequency, the percent block for quinidine is 33±6 ($10^{-6}$ M), 42±2 ($10^{-5}$ M), and 83±2 ($10^{-4}$ M), while the percent block for quinine is 10±3 ($10^{-6}$ M), 21±6 ($10^{-5}$ M), and 52±10 ($10^{-4}$ M). Quinidine (D-isomer) blocks $I_{Kr}$ 12.5 times greater than quinine (L-isomer). The current block for the two isomers is dose dependent with quinidine being an order of magnitude more potent than quinine. The difference in quinidine and quinine on cardiac electrophysiology may be clinically useful and may explain the higher incidence of proarrhythmia with torsade de pointes (toxic arrhythmia) seen with quinidine therapy as contrasted to quinine therapy.

Conclusions

The data shows that further chiral separation of quinidine initially gives two chromatographic peaks. The two peaks have distinctly different properties as to the inhibiting action on the potassium channel (IK$_r$) as well as on GI contractility (illeal step preparation). One eluent (peak b) has properties similar to quinidine in that it inhibits the potassium channel IK$_r$ in an analogous fashion to quinidine, while a second peak does not inhibit the IK$_r$ current (peak a). Both eluents effect the sodium channel similarly. The eluent that does not effect IK$_r$ does not increase illeal contractility. These results segregate two toxic effects of quinidine to one isomer (or a mixture of isomers), while leaving another free of potential cardiac and GI toxicity.

The invention and manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

We claim:

1. A stereoisomerically purified form of a compound selected from the group consisting of quinine and quinidine, wherein the stereoisomerically purified form has different effects on cardiac ion channels and on gastric motility compared to the stereoisomerically unpurified form of the compound, wherein the stereoisomerically purified form of a compound is selected from the group consisting of:

(1R)((2R,4R,8R)-8-vinylquinuclidin-2-yl)(6-methoxy(4-quinolyl))methan-1-ol;

(1R)((2R,4R,8S)-8-vinylquinuclidin-2-yl)(6-methoxy(4-quinolyl))methan-1-ol;

(1R)((2R,4S,8R)-8-vinylquinuclidin-2-yl)(6-methoxy(4-quinolyl))methan-1-ol;

(1R)((2R,4S,8S)-8-vinylquinuclidin-2-yl)(6-methoxy(4-quinolyl))methan-1-ol;

(1R)((2S,4R,8R)-8-vinylquinuclidin-2-yl)(6-methoxy(4-quinolyl))methan-1-ol;

(1R)((2S,4R,8S)-8-vinylquinuclidin-2-yl)(6-methoxy(4-quinolyl))methan-1-ol;

(1R)((2S,4S,8R)-8-vinylquinuclidin-2-yl)(6-methoxy(4-quinolyl))methan-1-ol;

(1R)((2S,4S,8S)-8-vinylquinuclidin-2-yl)(6-methoxy(4-quinolyl))methan-1-ol;

(1S)((2R,4R,8R)-8-vinylquinuclidin-2-yl)(6-methoxy(4-quinolyl))methan-1-ol;

(1S)((2R,4R,8S)-8-vinylquinuclidin-2-yl)(6-methoxy(4-quinolyl))methan-1-ol;

(1S)((2R,4S,8R)-8-vinylquinuclidin-2-yl)(6-methoxy(4-quinolyl))methan-1-ol;

(1S)((2R,4S,8S)-8-vinylquinuclidin-2-yl)(6-methoxy(4-quinolyl))methan-1-ol;

(1S)((2S,4R,8R)-8-vinylquinuclidin-2-yl)(6-methoxy(4-quinolyl))methan-1-ol;

(1S)((2S,4R,8S)-8-vinylquinuclidin-2-yl)(6-methoxy(4-quinolyl))methan-1-ol;

(1S)((2S,4S,8R)-8-vinylquinuclidin-2-yl)(6-methoxy(4-quinolyl))methan-1-ol;

(1S)((2S,4S,8S)-8-vinylquinuclidin-2-yl)(6-methoxy(4-quinolyl))methan-1-ol; and mixtures thereof.

2. The stereoisomerically purified form of claim 1 wherein the compound is quinidine.

3. The stereoisomerically purified form of quinidine of claim 2 having from one to seven stereoisomers of quinidine.

4. The stereoisomerically purified form of quinidine of claim 3 having less effect on $I_{Kr}$ than a stereoisomerically unpurified form of quinidine.

5. The stereoisomerically purified form of quinidine of claim 4 having less QT prolongation than a stereoisomerically unpurified form of quinidine.

6. The stereoisomerically purified form of quinidine of claim 5 having less Torsade de Pointes ventricular tachycardia effect than a stereoisomerically unpurified form of quinidine.

7. A composition suitable for the treatment of arrhythmia comprising the stereoisomerically purified form of quinidine of claim 3 and a pharmaceutically suitable excipient.

8. The stereoisomerically purified form of quinidine of claim 3 having a sodium channel effect similar to that of a stereoisomerically unpurified form of quinidine, having less effect on $I_{Kr}$ than that of a stereoisomerically unpurified form of quinidine, and having less gastrointestinal side-effects than a stereoisomerically unpurified form of quinidine.

9. A method for stereoisomerically purifying a compound, the compound selected from quinine and quinidine, the method comprising passing the compound through a chiral column and obtaining a stereoisomerically purified form of the compound, wherein the stereoisomerically purified form of the compound is selected from the group consisting of (1R)((2R,4R,8R)-8-vinylquinuclidin-2-yl)(6-methoxy(4-quinolyl))methan-1-ol;

(1R)((2R,4R,8S)-8-vinylquinuclidin-2-yl)(6-methoxy(4-quinolyl))methan-1-ol;

(1R)((2R,4S,8R)-8-vinylquinuclidin-2-yl)(6-methoxy(4-quinolyl))methan-1-ol;

(1R)((2R,4S,8S)-8-vinylquinuclidin-2-yl)(6-methoxy(4-quinolyl))methan-1-ol;

(1R)((2S,4R,8R)-8-vinylquinuclidin-2-yl)(6-methoxy(4-quinolyl))methan-1-ol;

(1R)((2S,4R,8S)-8-vinylquinuclidin-2-yl)(6-methoxy(4-quinolyl))methan-1-ol;

(1R)((2S,4S,8R)-8-vinylquinuclidin-2-yl)(6-methoxy(4-quinolyl))methan-1-ol;

(1R)((2S,4S,8S)-8-vinylquinuclidin-2-yl)(6-methoxy(4-quinolyl))methan-1-ol;

(1S)((2R,4R,8R)-8-vinylquinuclidin-2-yl)(6-methoxy(4-quinolyl))methan-1-ol;

(1S)((2R,4R,8S)-8-vinylquinuclidin-2-yl)(6-methoxy(4-quinolyl))methan-1-ol;

(1S)((2R,4S,8R)-8-vinylquinuclidin-2-yl)(6-methoxy(4-quinolyl))methan-1-ol;

(1S)((2R,4S,8S)-8-vinylquinuclidin-2-yl)(6-methoxy(4-quinolyl))methan-1-ol;

(1S)((2S,4R,8R)-8-vinylquinuclidin-2-yl)(6-methoxy(4-quinolyl))methan-1-ol;

(1S)((2S,4R,8S)-8-vinylquinuclidin-2-yl)(6-methoxy(4-quinolyl))methan-1-ol;

(1S)((2S,4S,8R)-8-vinylquinuclidin-2-yl)(6-methoxy(4-quinolyl))methan-1-ol;

(1S)((2S,4S,8S)-8-vinylquinuclidin-2-yl)(6-methoxy(4-quinolyl))methan-1-ol; and mixtures thereof.

10. The method of claim 9 wherein the compound is quinidine.

11. The method of claim 10 wherein the stereoisomerically purified form of quinidine has from one to seven stereoisomers of quinidine.

12. A method for treating cardiac arrhythmias in a patient having a need for such treatment comprising administering to the patient an effective amount of the stereoisomerically purified form of a compound of claim 1.

13. The method of claim 12 wherein the cardiac arrhythmia is selected from the group consisting of an atrial arrhythmia; a ventricular arrhythmia; or an atrial arrhythmia and a ventricular arrhythmia.

14. A method for treating malaria in a patient having a need for such treatment comprising administering to the patient an effective amount of the stereoisomerically purified form of a compound of claim 1.

15. The stereoisomerically purified form of a compound of claim 1 wherein the compound is quinine.

16. The stereoisomerically purified form of quinine of claim 15 having from one to seven stereoisomers of quinine.

17. The stereoisomerically purified form of quinine of claim 16 having less effect on $I_{Kr}$ than a stereoisomerically unpurified form of quinine and having less reduction of gastric motility than a stereoisomerically unpurified form of quinine.

18. A composition suitable for the treatment of malaria comprising the stereoisomerically purified form of quinidine of claim 17 and a pharmaceutically suitable excipient.

19. A stereoisomerically purified compound, or mixture of said compounds, according to claim 1, wherein the compound or compounds have less or no QT prolonging action, and wherein the compound or mixture compounds possess prokinetic GI effects, compared to the unpurified form of the compounds or mixture of compounds.

20. A stereoisomerically purified compound, or mixture of said compounds, according to claim 1, wherein the compound or compounds have the same, less or no QT prolonging action, wherein the compound or mixture compounds possess anti-arrhythmic action due to sodium channel blocking, and wherein the compound or mixture of compounds do not possess prokinetic GI action or a lesser degree of GI stimulation, compared to the unpurified form of the compounds or mixture of compounds.

* * * * *